(12) United States Patent
Shin et al.

(10) Patent No.: US 7,718,685 B2
(45) Date of Patent: May 18, 2010

(54) 4,5-BIS(4-METHOXYPHENYL)IMIDIZOLE COMPOUND INDUCING DIFFERENTIATION OF MYOBLASTS OR MUSCLE FIBERS AND PHARMACEUTICAL COMPOSITIONS INCLUDING SAID COMPOUND

(75) Inventors: In-Jae Shin, Kyungki-do (KR); Myung-Ryul Lee, Kyungki-do (KR); Darren Williams, Seoul (KR)

(73) Assignee: Industry-Academic Cooperation Foundation, Yonsei University (KR)

( * ) Notice: Subject to any disclaimer, the term of this patent is extended or adjusted under 35 U.S.C. 154(b) by 1155 days.

(21) Appl. No.: 11/337,145

(22) Filed: Jan. 20, 2006

(65) Prior Publication Data

US 2007/0123576 A1 May 31, 2007

(30) Foreign Application Priority Data

Nov. 25, 2005 (KR) ...................... 10-2005-0113315

(51) Int. Cl.
*A01N 43/50* (2006.01)
(52) U.S. Cl. .................................... 514/396; 548/343.5
(58) Field of Classification Search ................ 514/396; 548/343.5
See application file for complete search history.

(56) References Cited

U.S. PATENT DOCUMENTS 3,772,441 A * 11/1973 Lombardino ................ 514/400

OTHER PUBLICATIONS

"Dedifferentiation of Lineage-Committed Cells by a Small Molecule"; Authors: Shuibing Chen, et al.; J. Am. Chem. Soc., vol. 126, No. 2; American Chemical Society; 2004; 5 pages.

"Small Molecules that Induce Cardiomyogenesis in Empryonic Stem Cells"; Authors: Xu Wu, et al.; J. Am,. Chem. Soc., vol. 126, No. 6, American Chemical Society; 2004; 6 pages.

"A Small Molecule with Osteogenesis-Inducing Activity in Multipotent Mesenchymal Progenitor Cells"; Authors: Xu Wu, et al.; J. AM. Chem. Soc., vol. 124, No. 49; American Chemical Society; 2002; 10 pages.

"Myoseverin, a microtubule-binding molecule with novel cellular effects"; Authors: Gustavo R. Rosania, et al.; Research Articles; Nature Biotechnology, vol. 18; Nature America Inc.; Mar. 2000; pp. 304-308.

* cited by examiner

*Primary Examiner*—Kamal A Saeed
*Assistant Examiner*—Valerie Rodriguez-Garcia
(74) *Attorney, Agent, or Firm*—Cantor Colburn LLP

(57) ABSTRACT

The present invention relates to 4,5-bis(4-methoxyphenyl) imidazole compound inducing differentiation of myoblasts or muscle fibers into neuron cells and a pharmaceutical composition including said compound. More specifically, it relates to 2-(2-fluorenyl)-4,5-bis(4-methoxyphenyl)imidazole that induces differentiation of myoblasts or muscle fibers, all pharmaceutically acceptable isomers, salts, hydrates, solvates and prodrug thereof, and a pharmaceutical composition including said compound.

11 Claims, 3 Drawing Sheets

Muscle fiber → Neurodazine 1 or 2 → Differentiation into neuron cells

4,5-BIS(4-METHOXYPHENYL)IMIDIZOLE COMPOUND INDUCING DIFFERENTIATION OF MYOBLASTS OR MUSCLE FIBERS AND PHARMACEUTICAL COMPOSITIONS INCLUDING SAID COMPOUND

FIELD OF THE INVENTION

The present invention relates to compounds inducing differentiation of myoblasts or muscle fibers into neuron cells, pharmaceutical composition including said compounds, a method for inducing neuron differentiation and a screening method for identifying additional compounds useful for inducing neuron differentiation. More specifically, it relates to compounds containing an imidazole scaffold that are useful for neuron differentiation from myoblasts or muscle fibers. In some embodiments, a pharmaceutical composition comprising imidazole derivatives is provided. In other embodiments, methods for differentiating myoblasts or muscle fibers into neuron cells are provided. Furthermore, screening methods to identify additional compounds useful for inducing neuron differentiation from myoblasts or muscle fibers are also provided.

BACKGROUND OF THE INVENTION

In mammals, damaged neuron cells are not regenerated and their damage causes neurodegenerative disorders, such as stroke, spinal cord injury, Parkinson's and Alzheimer's diseases (*J. Neurochem.* 2005, 93, 1412 and *Neuron* 2003, 39, 889). Recent advances in stem cell biology offer the prospect of new therapeutic approaches for treating a number of diseases including cardiovascular disease, neurodegenerative disease, musculoskeletal disease, diabetes and cancer (Committee on the Biological and Biomedical Applications of Stem Cell Research, *Stem Cells and the Future of Regenerative Medicine* 2002, the National Academies Press, Washington, D.C.). However, these approaches require identification of renewable cell sources of engraftable functional cells, precise control of differentiation, suppression of the immune response of differentiated cells and prevention of cancer induction by undifferentiated stem cells (*Curr. Top. Med. Chem.* 2005, 5, 383 and *Biotechnol.* 2004, 22, 833).

Alternatively, chemical approaches using small molecules that induce neuron differentiation from easily available cells or tissues such as myoblasts or muscle fibers have great potential (*Nature* 2002, 416, 485, *Nature* 2002, 418, 41 and *Science* 2004 303, 1669). Several examples of the differentiation of mammalian cells into specific cell types using small molecules have been reported. For example, osteoblasts are differentiated from embryogenic mesoderm fibroblasts (C3H10T1/2) using Purmorphamine (*J. Am. Chem. Soc.* 2002, 124, 14520). In addition, cardiac muscle cells and neuron cells are differentiated from embryonic stem cells (P19) by Cardiogenols and TWS-119, respectively (*J. Am. Chem. Soc.* 2004, 126, 1590 and *Proc. Natl. Acad. Sci. USA* 2003, 100, 7632). Thus, compounds that induce neuron differentiation may be very useful for producing a source of neuron cells for trials of transplantation therapies for neurodegenerative disorders.

Therefore, there is a need in the art for compositions and methods for inducing differentiation of easily available cells or tissues into neuron cells. The developed small molecule inducers not only provide valuable information on the molecular mechanism of neuron differentiation but may also, ultimately, allow in vivo neuron regeneration. The present invention satisfies these and other needs.

SUMMARY OF THE INVENTION

The present invention relates to new compositions and methods for inducing the differentiation of myoblasts or muscle fibers into neuron cells. Thus, the said compounds can be used for producing neuron cells from myoblasts or muscle fibers to treat neurodegenerative diseases.

The first object of the present invention is to provide compounds that induce neuron differentiation from myoblasts or muscle fibers.

The second object of the invention is to provide pharmaceutical compositions comprising the said compounds as an active ingredient for the differentiation of neuron cells from myoblasts or muscle fibers to treat medical dysfunctions and diseases caused by damaged neuron cells. The said compounds include all pharmaceutically acceptable isomers, salts, hydrates, solvates and prodrugs thereof.

The third object of the invention is to provide methods for inducing neuron differentiation from myoblasts or muscle fibers. When the said compounds are incubated with mammalian myoblasts or muscle fibers, they differentiate into neuron cells.

The fourth object of the invention is to provide screening methods to identify additional compounds useful for inducing neuron differentiation from myoblasts or muscle fibers.

Other embodiments of the present invention will become apparent from the following descriptions.

DETAILED DESCRIPTION OF THE INVENTION

Figure 1:
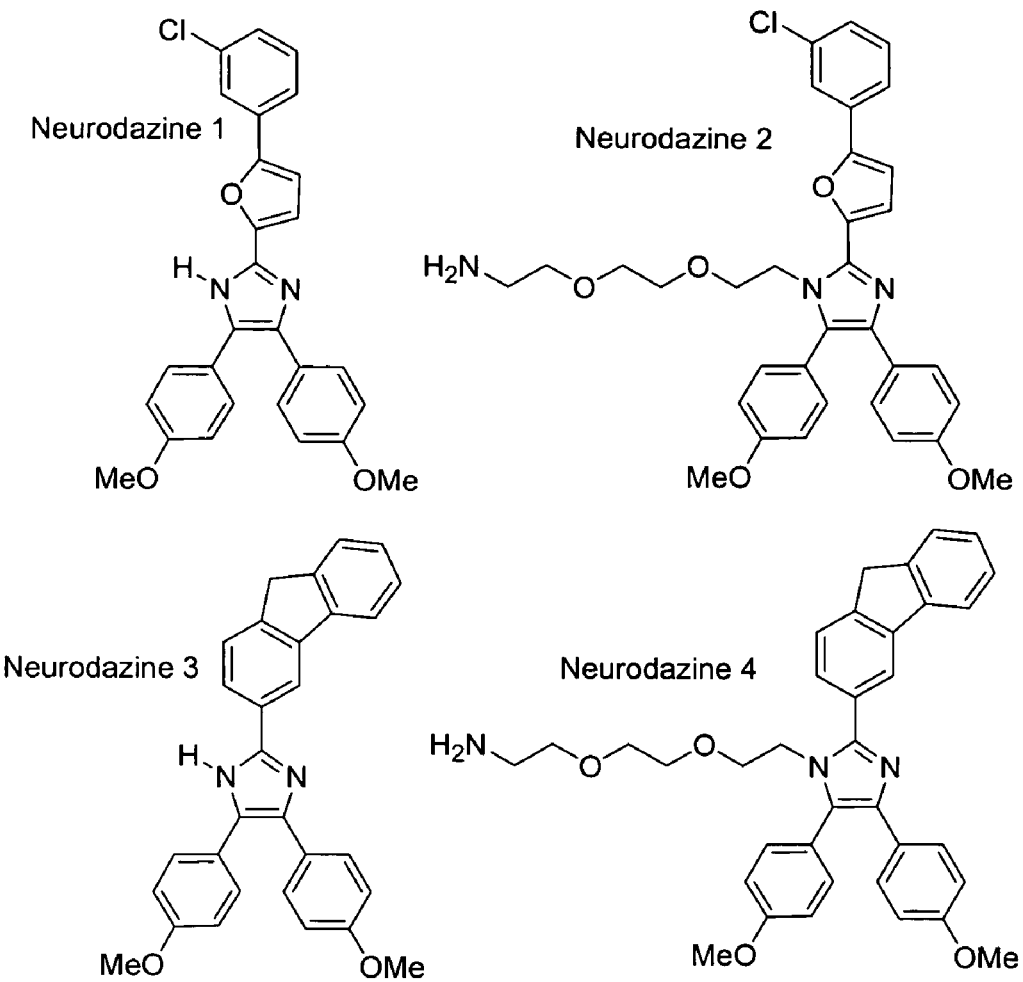
FIG. 1. Structures of Neurodazines 1-4.
Figure 2:
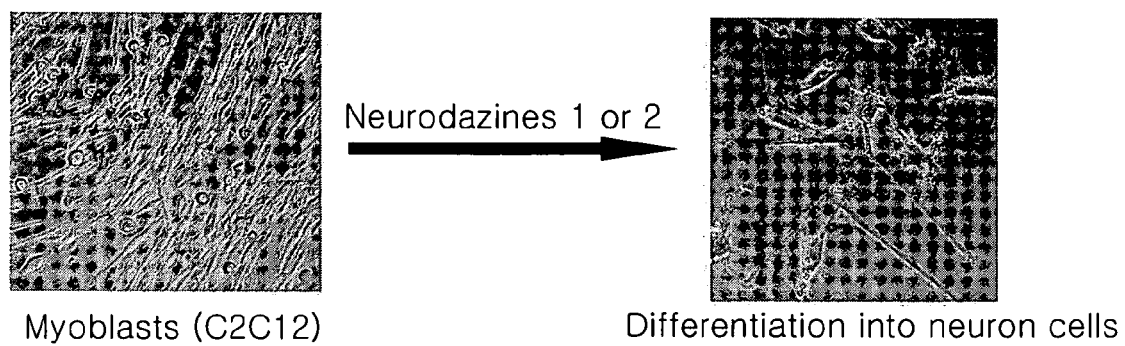
FIG. 2. Differentiated neuron cells from myoblasts by Neurodazine 1.
Figure 3:
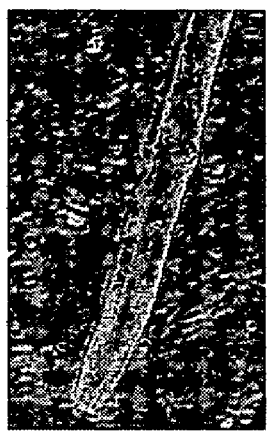
FIG. 3. Differentiated neuron cells from muscle fibers by Neurodazine 1.
Figure 3:
Figure 3:
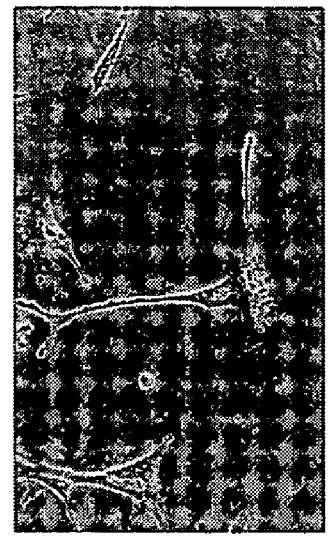

The present invention provides novel imidazole derivatives with the following Formula (I):

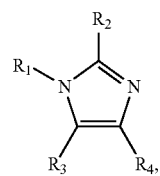

Formula (I)

wherein, $R_1$ is a functional group including, but not limited to, hydrogen, $C_{0-4}$alkylaryl, $C_{1-6}$alkyl, $C_{3-8}$cycloalkyl or —[(CH$_2$)$_2$—O]$_{0-3}$—(CH$_2$)$_2$NH$_2$;

$R_2$ is a functional group including, but not limited to, alkyl, $C_{3-8}$cycloalkyl, $C_{0-4}$alkylaryl or alkenylaryl;

$R_3$ is a functional group including, but not limited to, alkyl, $C_{3-8}$cycloalkyl, $C_{0-4}$alkylaryl or alkenylaryl;

$R_4$ is functional group including, but not limited to, alkyl, $C_{3-8}$cycloalkyl, $C_{0-4}$alkylaryl or alkenylaryl.

The preferred compounds include derivatives in which $R_1$ is a functional group including, but not limited to, the following:

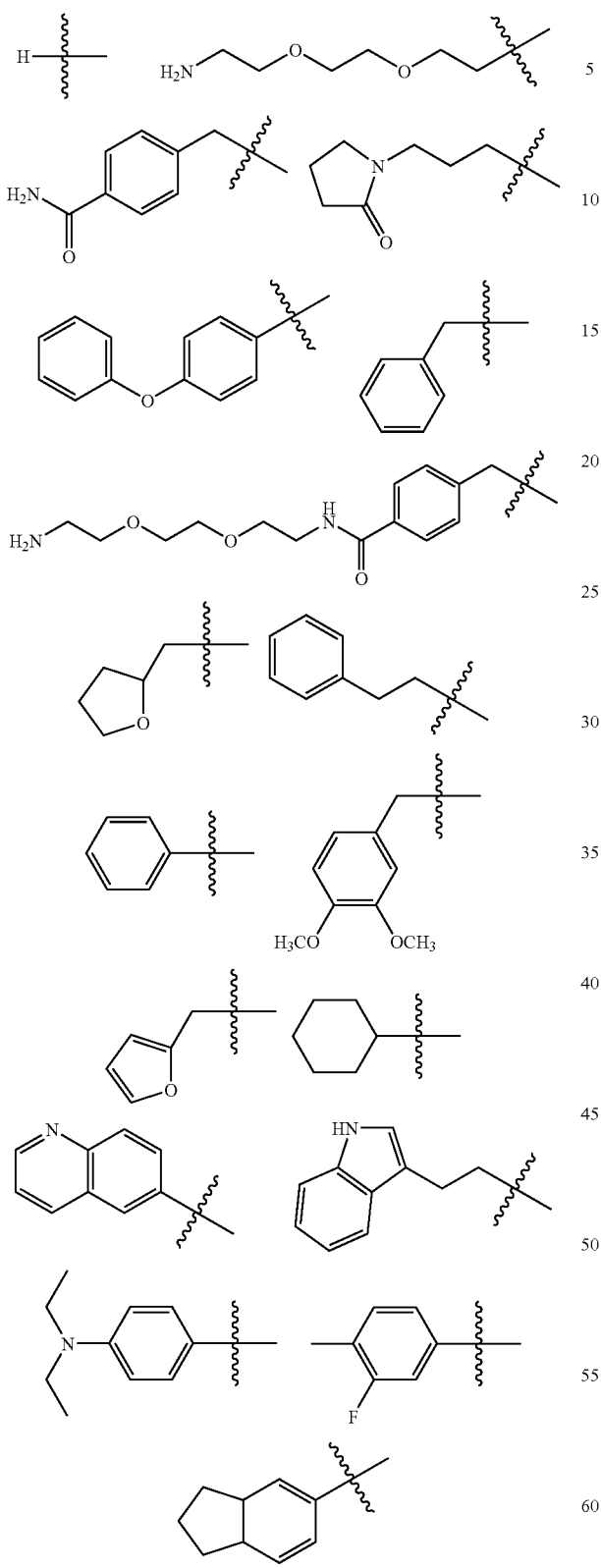
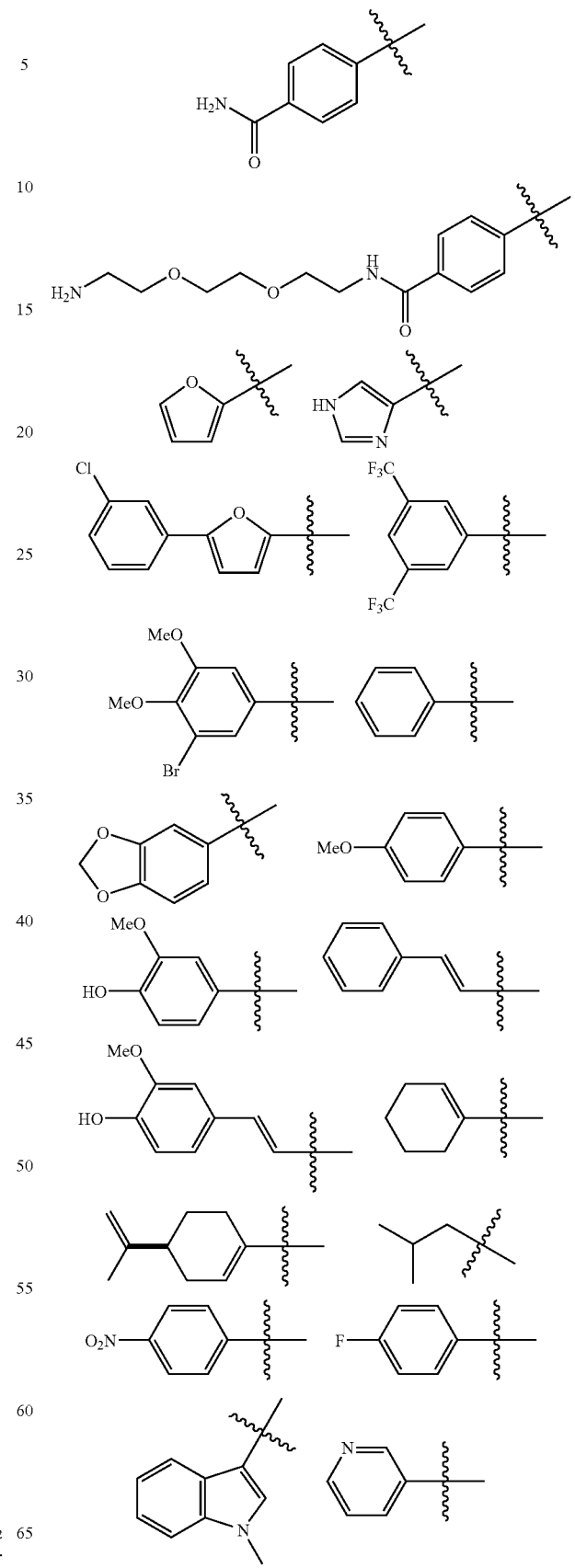
The preferred compounds include derivatives in which $R_2$ is a functional group including, but not limited to, the following:

-continued
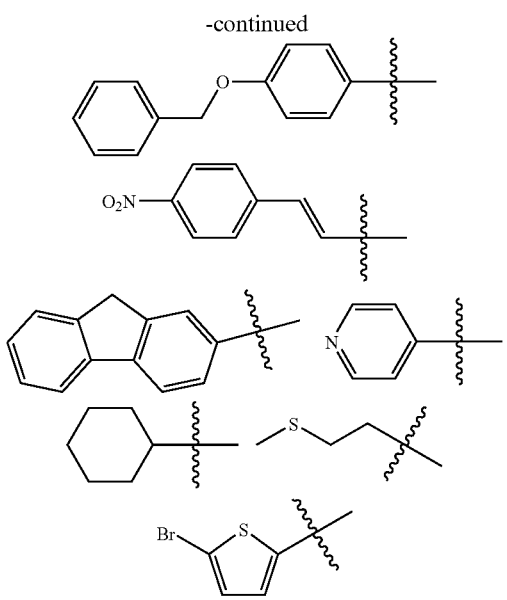
The preferred compounds include derivatives in which $R_3$ and $R_4$ are functional groups including, but not limited to, the following:
$(R_3, R_4) =$ 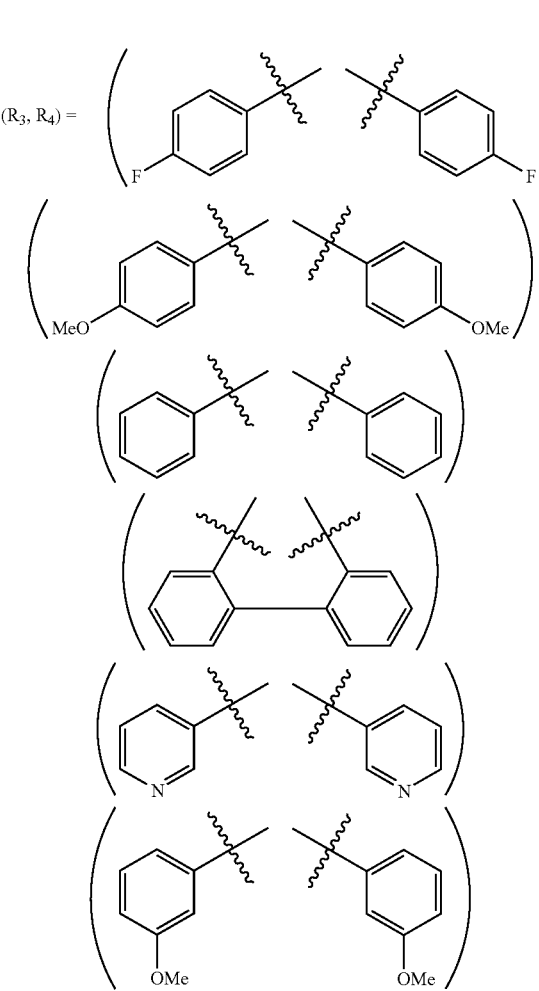
-continued
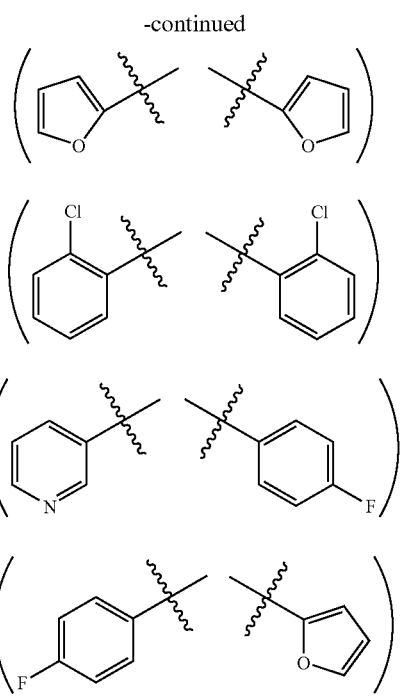
More preferred compounds of the present invention include, but not limited to, the following compounds:
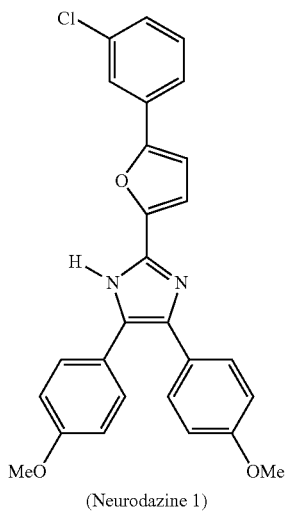
Compound 1
(Neurodazine 1)

-continued

Compound 2

(Neurodazine 2)

Compound 3

Compound 4

Compound 5

Compound 6

Compound 7

(Neurodazine 3)

Compound 8

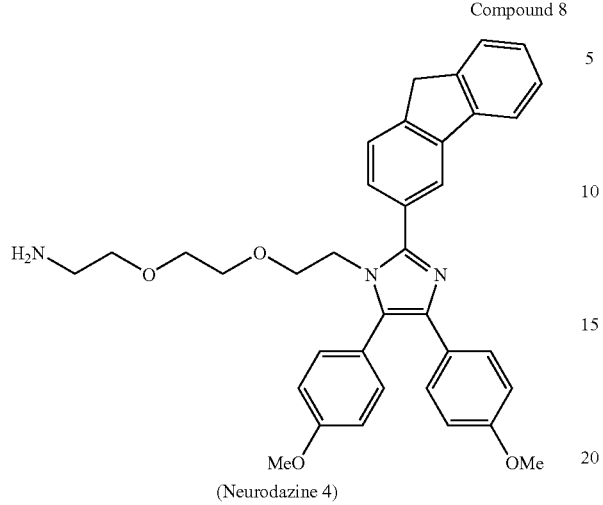

(Neurodazine 4)

Particularly preferred compounds have the following structures:

Neurodazine 1

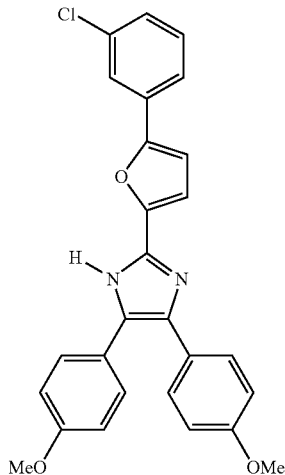

Neurodazine 2

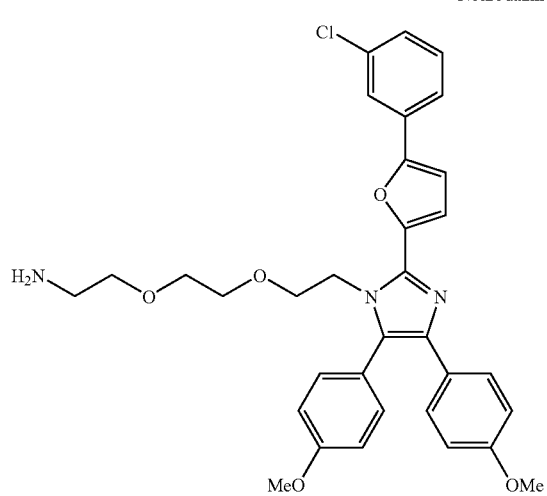

Neurodazine 3

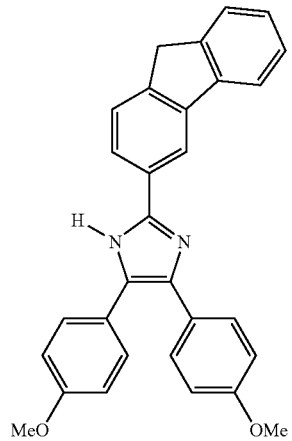

Neurodazine 4

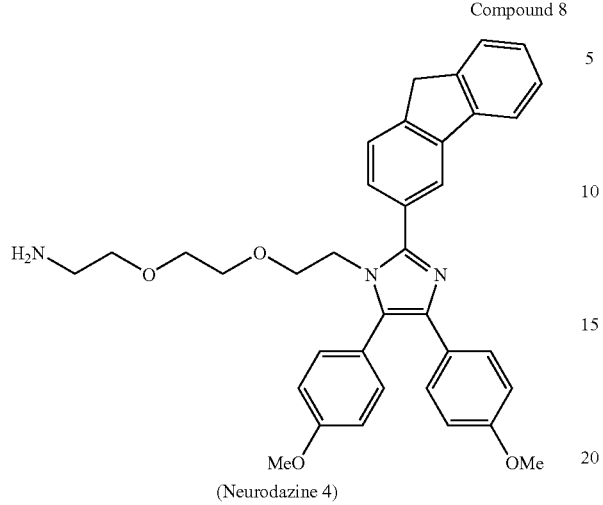

The present invention also provides all pharmaceutically acceptable isomers, salts, hydrates, solvates and prodrugs thereof.

The present invention also provides the method of inducing differentiation of myoblasts or muscle fibers into neuron cells by treating myoblasts and muscle fibers with a compound of the present invention, whereby the myoblasts and muscle fibers differentiate into neuron cells.

The present invention also provides the screening method for identifying additional compounds useful for inducing neuron differentiation, wherein myoblasts and muscle fibers are incubated with a compound of the present invention and detected.

Methods for Inducing Neuron Differentiation from Myoblasts or Muscle Fibers

The compositions of the present invention can be used to induce neuron differentiation from myoblasts or muscle fibers. Myoblasts are incubated with various concentrations of a compound of Formula I (or a composition thereof), whereupon the cells differentiate into neuron cells. In addition, satellite muscle precursor cells produced from isolated skeletal muscle fibers are treated with various concentrations of a compound of Formula I (or a composition thereof), whereupon the precursor cells differentiate into neuron cells. Alternatively, muscle fibers isolated from skeletal muscle are initially treated with Myoseverin. Myoseverin causes the muscle fibers to hypercontract with discrete fiber fragments, satellite cells and other discrete cellular entities appearing around the fiber exterior, similar to their effect on differentiating myotubes from the murine myoblasts (C2C12) (*Nat. Biotechnol.* 2000, 18, 304). They are re-plated and incubated with various concentrations of a compound of Formula I (or a composition thereof), whereupon they differentiate into neuron cells.

The concentration of a compound of Formula I, such as Neurodazines 1-4, can be adjusted to facilitate the differentiation of myoblasts or muscle fibers into neuron cells. Typically, Neurodazines 1-4 are incubated with the cells between 0.5 µM to 20 µM, the most typically at about 1 µM.

Suitable myoblasts can be derived from any mammal such as mice, rats, guinea pigs, rabbits, dogs, cats, pigs, sheep, horses, cows, goats, chimpanzees and humans. Myoblasts refers to primary cells derived from a muscle sample (either satellite cells surrounding the muscle fiber or the myogenic cells that arise from treating the muscle fibers with Myoseverin), or the commercially available cell lines transformed in culture e.g. C2C12. Myoblasts are cultured under conditions known to be optimal for cell growth. Such conditions include a temperature of 37° C. with 5% $CO_2$ in air atmosphere. Cells are cultured on plastic dishes, flasks, or roller bottles according to the methods of the present invention. Suitable culture vessels include multi-well plates, Petri dishes, tissue culture tubes, flasks, roller bottles, and so on.

Culture media for the present invention are available as packed, premixed powders or pre-sterilized solutions. Commonly used media include MEM-α, DME, RPMI 1640, DMEM, Ham's F-10, Iscove's complete media or McCoy's Medium. Typically, RPMI 1640, DMEM and Ham's F-10 are used in the methods of the invention. The culture media are supplemented with 5-20% serum, typically heat inactivated serum. Typically, 10% fetal bovine serum (FBS) is used in the methods of the invention. The culture medium is generally buffered to maintain the cells at a pH 7.2-7.4. Other supplements to media typically include antibiotics, amino acids, and sugars, and growth factors.

One aspect of the present invention provides methods for differentiating myoblasts or muscle fibers into neuron cells. In an exemplary embodiment, myoblasts are incubated with a composition comprising Neurodazines 1-4, and differentiate into neuron cells. Differentiation of myoblasts into neuron cells can be detected by any means known in the art including, e.g., detecting expression of cell type-specific marker proteins, observing morphological changes of cells and detecting fluorescent intensity of cells after treatment with FM1-43 in the presence of 100 mM KCl.

For instance, neuron cells typically express the following marker proteins: neuron-specific enolase, neurofilament 200 and neuron-specific βIII-tubulin. Expression of cell-specific markers may be detected by measuring the level of expression of the cell-specific proteins. The level of particular cell-specific markers can be conveniently be measured using immunoassays such as immunocytochemical analysis, western blotting analysis, ELISA and so on with an antibody that selectively binds to the particular cell-specific markers. Detection of the protein using protein-specific antibodies in immunoassays is known to those of skill in the art (Harlow & Lane, Antibodies: A Laboratory Manual (1988)).

Morphological changes of cells by neurite formation are indicia of neuron differentiation and can be detected using any methods known to those of skill in the art. Typically, morphological changes of the cells are visually detected using a light microscope.

Neuron differentiation may be also detected by measuring fluorescent intensity of cells after incubation with FM1-43 in the presence of 100 mM KCl. At a high concentration of $K^+$, FM1-43 enters the neuron cells when the synaptic vesicles are recycled back into the neuron after depolarization. Thus, differentiated neuron cells exhibit a high fluorescence signal (Genes & Development 2004, 18, 889).

Methods of Screening Compounds that Induce Neuron Differentiation from Myoblasts or Muscle Fibers One embodiment of the present invention provides a screening method for additional compounds that induce neuron differentiation from myoblasts or muscle fibers. The myoblasts are incubated with a test compound that may possess the potential to induce neuron differentiation. Differentiation of myoblasts into neuron cells can be detected by observing morphological changes of cells using a light microscope or measuring fluorescent intensity of cells after treatment with FM1-43 in the presence of 100 mM KCl. To determine whether myoblasts have differentiated into neuron cells, the myoblasts are cultured in at least two separate cell culture media, each of which induces differentiation of myoblasts into neuron cells. Induction of differentiation of myoblasts into neuron cells identifies the test compound as a "hit" that induces neuron differentiation.

In one preferred embodiment, high-throughput screening methods involve providing a library containing a large number of potential therapeutic compounds. Such combinatorial chemical libraries are then screened in one or more assays to identify those library members that display a neuron differentiation inducing activity. The compounds thus identified can serve as conventional lead compounds or can be used as potential or actual therapeutics.

Methods of Treatment

Another embodiment of the invention provides methods of treating individuals with diseases or disorders which can be treated by administration of differentiated cells. In this embodiment, myoblasts are incubated with a compound of Formula I (e.g. Neurodazines 1-4 or compositions thereof), whereupon the myoblasts differentiate into neuron cells. Alternatively, satellite muscle precursor cells produced from isolated muscle fibers are treated with a compound of Formula I (e.g. Neurodazines 1-4 or compositions thereof), whereupon the precursor cells differentiate into neuron cells. In addition, muscle precursor cells produced from muscle fibers after treatment with Myoseverin are contacted with a compound of Formula I (e.g. Neurodazines 1-4 or compositions thereof), whereupon the precursor cells differentiate into neuron cells. The differentiated neuron cells are then administrated to an individual in need of such treatment.

The following examples are offered to illustrate, but not limited to, the claimed invention.

EXAMPLE 1

Synthesis of 2-{2-[5-(3-chlorophenyl)]furanyl}-4,5-bis(4-methoxyphenyl)imidazole (Compound 1 or Neurodazine 1)

5-(3-Chlorophenyl)furfural (10 mg, 0.048 mmol), ammonium acetate (44 mg, 0.57 mmol), and 4,4'-dimethoxybenzil (13 mg, 0.048 mmol) was suspended in acetic acid (500 µL), and then the suspension was heated to 100° C. After stirring for 6 h, the reaction mixture was diluted with ethyl acetate and washed with saturated $NaHCO_3$ and brine. The organic layer was concentrated in vacuo. The crude product was purified by flash column chromatography.

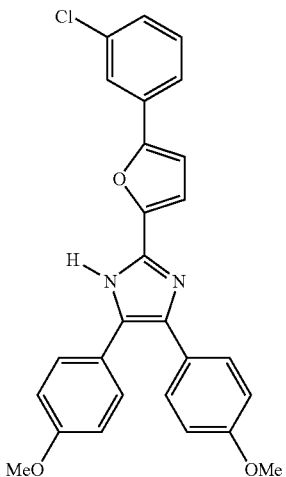

Compound 1

¹H NMR (500 MHz, CDCl₃) δ 12.85 (s, 1H), 7.96 (s, 1H), 7.77 (d, 1H, J=7.5 Hz), 7.50-7.35 (m, 5H), 7.28 (d, 1H, J=7.5 Hz), 7.17 (s, 1H), 7.02 (s, 1H), 6.98-6.83 (m, 4H), 3.72 (s, 6H).

¹³C NMR (125 MHz, CDCl₃) δ 158.4, 150.9, 146.0, 137.5, 133.9, 131.9, 130.5, 129.5, 128.5, 127.1, 123.0, 122.1, 113.8, 109.3, 108.9, 55.02.

MALDI-TOF-MS calcd for $C_{27}H_{21}ClN_2O_3$ (M+H)⁺ 457.12, found 457.12.

EXAMPLE 2

Synthesis of 2-{2-[5-(3-chlorophenyl)]furanyl}-4,5-bisphenyl imidazole (Compound 3)

5-(3-Chlorophenyl)furfural (10 mg, 0.048 mmol), ammonium acetate (44 mg, 0.57 mmol), and benzil (10 mg, 0.048 mmol) was suspended in acetic acid (500 μL), and then the suspension was heated to 100° C. After stirring for 6 h, the reaction mixture was diluted with ethyl acetate and washed with saturated NaHCO₃ and brine. The organic layer was concentrated in vacuo. The crude product was purified by flash column chromatography.

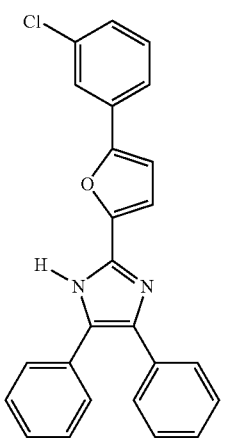

Compound 3

¹H NMR (500 MHz, CDCl₃) δ 13.02 (s, 1H), 8.01 (s, 1H), 7.85 (d, 1H, J=7.5 Hz), 7.61-7.50 (m, 4H), 7.49-7.43 (m, 3H), 7.42-7.20 (m, 6H), 7.10 (s, 1H).

¹³C NMR (125 MHz, CDCl₃) δ 151.0, 145.7, 138.1, 137.4, 134.7, 133.8, 131.8, 130.8, 130.6, 128.6, 128.1, 127.9, 127.2, 127.0, 126.6, 123.0, 122.2, 109.3.

MALDI-TOF-MS calcd for $C_{25}H_{17}ClN_2O$ (M+H)⁺ 397.10, found 397.10.

EXAMPLE 3

Synthesis of 2-(2-fluorenyl)-4,5-bis(4-fluorophenyl)imidazole (Compound 5)

2-Fluorenecarboxaldehyde (9 mg, 0.048 mmol), ammonium acetate (44 mg, 0.57 mmol), and 4,4'-difluorobenzil (12 mg, 0.048 mmol) was suspended in acetic acid (500 μL), and then the suspension was heated to 100° C. After stirring for 6 h, the reaction mixture was diluted with ethyl acetate and washed with saturated NaHCO₃ and brine. The organic layer was concentrated in vacuo. The crude product was purified by flash column chromatography.

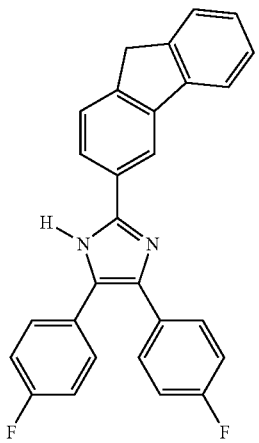

Compound 5

¹H NMR (500 MHz, CDCl₃) δ 12.74 (s, 1H), 8.33 (s, 1H), 8.14 (d, 1H, J=7.5 Hz), 7.98 (d, 1H, J=7.5 Hz), 7.91 (d, 1H, J=7.0 Hz), 7.64-7.52 (m, 5H), 7.39 (dd, 1H, J=6.5, 7.5 Hz), 7.37-7.12 (m, 5H), 4.0 (s, 2H).

¹³C NMR (125 MHz, CDCl₃) δ 161.3 (d, 243 Hz), 145.9, 143.4, 143.3, 141.2, 140.7, 136.2, 131.5, 130.3, 129.0, 128.7, 126.9, 126.8, 125.1, 124.0, 121.8, 120.1, 115.3, 36.4.

MALDI-TOF-MS calcd for $C_{28}H_{18}F_2N_2$ (M+H)⁺ 421.14, found 421.14.

EXAMPLE 4

Synthesis of 2-(2-fluorenyl)-4,5-bis(4-methoxyphenyl)imidazole (Compound 7 or Neurodazine 3)

2-Fluorenecarboxaldehyde (9 mg, 0.048 mmol), ammonium acetate (44 mg, 0.57 mmol), and 4,4'-dimethoxybenzil (13 mg, 0.048 mmol) was suspended in acetic acid (500 μL), and then the suspension was heated to 100° C. After stirring for 6 h, the reaction mixture was diluted with ethyl acetate and washed with saturated NaHCO₃ and brine. The organic layer was concentrated in vacuo. The crude product was purified by flash column chromatography.

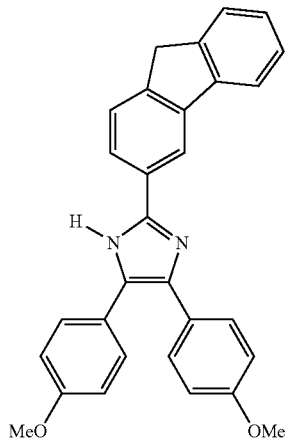

Compound 7

¹H NMR (500 MHz, CDCl₃) δ 12.53 (s, 1H), 8.30 (s, 1H), 8.12 (d, 1H, J=7.5 Hz), 7.93 (d, 1H, J=7.5 Hz), 7.87 (d, 1H, J=6.5 Hz), 7.58-7.48 (m, 3H), 7.4-7.40 (m, 2H), 7.35 (dd, 1H, J=6.1, 6.7 Hz), 7.31-7.24 (m, 2H), 6.98 (d, 2H, J=7 Hz), 6.86 (d, 2H, J=7.5 Hz), 3.97 (s, 2H), 3.76 (s, 3H), 3.72 (s, 3H).

¹³C NMR (125 MHz, CDCl₃) δ 159.4, 158.6, 145.9, 144.1, 144.0, 141.5, 141.4, 137.2, 130.3, 129.7, 128.9, 128.6, 127.8, 127.5, 125.7, 124.6, 124.2, 122.3, 120.7, 114.7, 114.2, 55.8, 55.6, 37.1.

MALDI-TOF-MS calcd for $C_{30}H_{24}N_2O_2$ (M+H)⁺ 445.18, found 445.18.

EXAMPLE 5

Synthesis of 1-(8-amino-3,6-dioxaoctyl)-2-{2-[5-(3-chlorophenyl)]furanyl}-4,5-bis(4-methoxyphenyl) imidazole (Compound 2 or Neurodazine 2)

A solution of 4-nitrophenyl chloroformate (0.8 g, 4 mmol) in CH₂Cl₂ was added to a Wang resin (1 mmol) in CH₂Cl₂ (9 mL) and pyridine (3 mL). After shaking for 12 h, the resin was washed with 10% dimethylformamide (DMF) in CH₂Cl₂. A solution of 2,2'-(ethylenedioxy)bisethylenediamine (1.5 g, 10 mmol) and diisopropylethylamine (0.6 g, 5 mmol) in DMF was added to the resin. After shaking for 12 h, the resin was washed with DMF. The resin (7 μmol), 5-(3-chlorophenyl) furfural (14 mg, 0.07 mmol), ammonium acetate (22 mg, 0.28 mmol) and 4,4'-dimethoxybenzil (19 mg, 0.07 mmol) was placed in a reaction vial and suspended in acetic acid (300 μL). The reaction vial was placed in a heat block on a shaker at 100° C. The reaction vial was shaken for 5 h. The resin was filtered and washed with DMF, MeOH, and CH₂Cl₂ several times. The desired compound was cleaved from a solid support by treatment with trifluoroacetic acid (TFA) for 1.5 h. The crude product was directly purified by preparative RP-HPLC with a gradient of 5-100% CH₃CN in water (0.1% TFA) over 85 min.

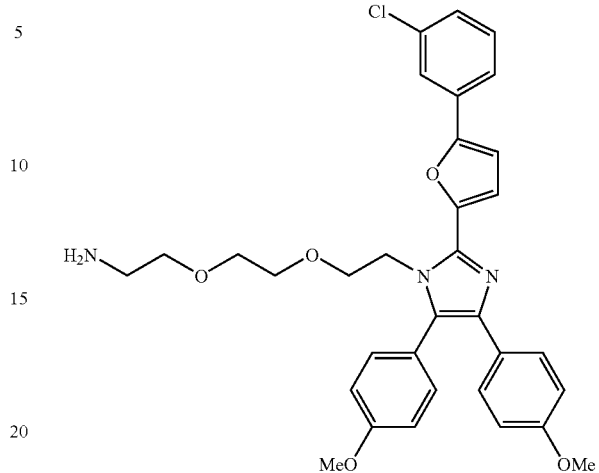

Compound 2

¹H NMR (500 MHz, CDCl₃) δ 7.94 (s, 1H), 7.83 (d, 1H, J=8.0 Hz), 7.53 (dd, 1H, J=7.5, 8.0 Hz), 7.47-7.39 (m, 5H), 7.38-7.31 (m, 2H), 7.12 (d, 2H, J=8.0 Hz), 6.89 (d, 2H, J=8.5 Hz), 4.38-4.32 (m, 2H), 3.84 (s, 3H), 3.72 (s, 3H), 3.62 (t, 2H, J=4.3 Hz), 3.47 (t, 2H, J=4.3 Hz), 3.44-3.37 (m, 4H), 2.92-2.84 (m, 2H).

¹³C NMR (125 MHz, CDCl₃) δ 160.0, 158.9, 153.1, 141.4, 135.7, 133.9, 133.5, 132.8, 131.0, 130.9, 129.8, 128.3, 128.1, 123.4, 122.5, 119.6, 115.2, 114.6, 113.8, 109.5, 69.5, 69.3, 68.5, 66.5, 55.1, 55.0, 45.1, 38.3.

MALDI-TOF-MS calcd for $C_{33}H_{34}ClN_3O_5$ (M+H)⁺ 588.22, found 588.22.

EXAMPLE 6

Synthesis of 1-(8-amino-3,6-dioxaoctyl)-2-{2-[5-(3-chlorophenyl)]furanyl}-4,5-bisphenyl imidazole (Compound 4)

A solution of 4-nitrophenyl chloroformate (0.8 g, 4 mmol) in CH₂Cl₂ was added to a Wang resin (1 mmol) in CH₂Cl₂ (9 mL) and pyridine (3 mL). After shaking for 12 h, the resin was washed with 10% dimethylformamide (DMF) in CH₂Cl₂. A solution of 2,2'-(ethylenedioxy)bisethylenediamine (1.5 g, 10 mmol) and diisopropylethylamine (0.6 g, 5 mmol) in DMF was added to the resin. After shaking for 12 h, the resin was washed with DMF. The resin (7 μmol), 5-(3-chlorophenyl) furfural (14 mg, 0.07 mmol), ammonium acetate (22 mg, 0.28 mmol) and benzil (15 mg, 0.07 mmol) was placed in a reaction vial and suspended in acetic acid (300 μL). The reaction vial was placed in a heat block on a shaker at 100° C. The reaction vial was shaken for 5 h. The resin was filtered and washed with DMF, MeOH, and CH₂Cl₂ several times. The desired compound was cleaved from a solid support by treatment with trifluoroacetic acid (TFA) for 1.5 h. The crude product was directly purified by preparative RP-HPLC with a gradient of 5-100% CH₃CN in water (0.1% TFA) over 85 min.

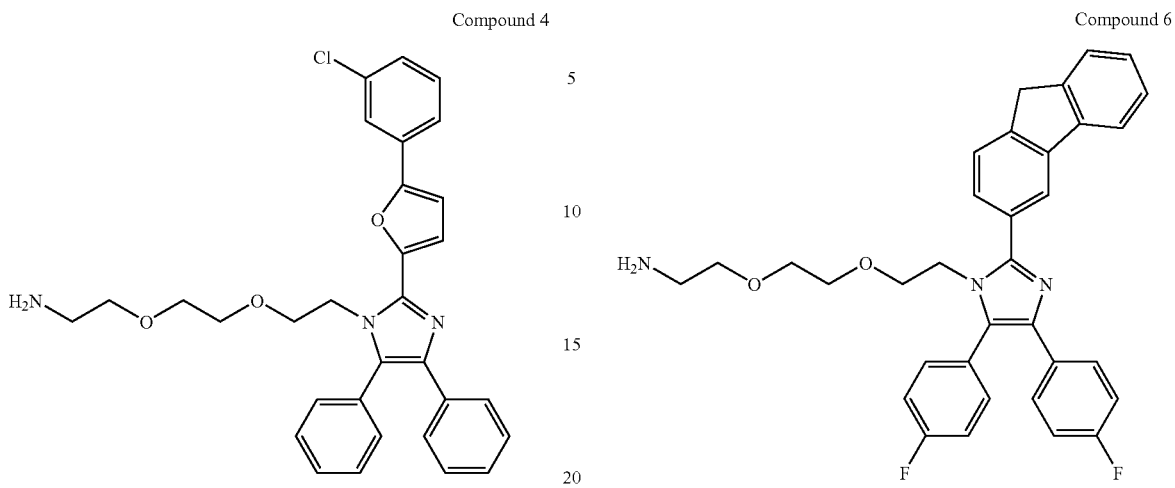

Compound 4

Compound 6

¹H NMR (500 MHz, CDCl₃) δ 7.92 (s, 1H), 7.81 (d, 1H, J=7.5 Hz), 7.61-7.55 (m, 3H), 7.54-7.47 (m, 3H), 7.45-7.35 (m, 5H), 7.31-7.20 (m, 3H), 4.40-4.32 (m, 2H), 3.61 (t, 2H, J=4.9 Hz), 3.46 (t, 2H, J=4.3 Hz), 3.43-3.35 (m, 4H), 2.92-2.83 (m, 2H).

¹³C NMR (125 MHz, CDCl₃) δ 152.8, 142.7, 136.8, 134.8, 134.0, 131.4, 130.9, 130.8, 129.6, 129.2, 128.6, 128.3, 128.0, 127.5, 126.8, 123.4, 122.4, 114.4, 109.5, 69.6, 69.4, 68.7, 66.6, 45.0, 38.4.

MALDI-TOF-MS calcd for $C_{31}H_{30}ClN_3O_3$ (M+H)⁺ 528.20, found 528.20.

EXAMPLE 7

Synthesis of 1-(8-amino-3,6-dioxaoctyl)-2-(2-fluorenyl)-4,5-bis(4-fluorophenyl)imidazole (Compound 6)

A solution of 4-nitrophenyl chloroformate (0.8 g, 4 mmol) in CH₂Cl₂ was added to a Wang resin (1 mmol) in CH₂Cl₂ (9 mL) and pyridine (3 mL). After shaking for 12 h, the resin was washed with 10% dimethylformamide (DMF) in CH₂Cl₂. A solution of 2,2'-(ethylenedioxy)bisethylenediamine (1.5 g, 10 mmol) and diisopropylethylamine (0.6 g, 5 mmol) in DMF was added to the resin. After shaking for 12 h, the resin was washed with DMF. The resin (7 μmol), 2-fluorenecarboxaldehyde (13 mg, 0.07 mmol), ammonium acetate (22 mg, 0.28 mmol) and 4,4'-difluorobenzil (17 mg, 0.07 mmol) was placed in a reaction vial and suspended in acetic acid (300 μL). The reaction vial was placed in a heat block on a shaker at 100° C. The reaction vial was shaken for 5 h. The resin was filtered and washed with DMF, MeOH, and CH₂Cl₂ several times. The desired compound was cleaved from a solid support by treatment with trifluoroacetic acid (TFA) for 1.5 h. The crude product was directly purified by preparative RP-HPLC with a gradient of 5-100% CH₃CN in water (0.1% TFA) over 85 min.

¹H NMR (500 MHz, CDCl₃) δ 8.07-7.93 (m, 3H), 7.81 (d, 1H, J=7.5 Hz), 7.62 (d, 1H, J=6.5 Hz), 7.59-7.52 (m, 2H), 7.48-7.32 (m, 5H), 7.11-7.03 (m, 2H), 4.18-4.10 (m, 2H), 4.02 (s, 2H), 3.33-3.17 (m, 8H), 2.55 (t, 2H, J=4.3 Hz).

¹³C NMR (125 MHz, CDCl₃) δ 162.5 (d, 195 Hz), 160.6 (d, 193 Hz), 147.6, 143.4, 143.2, 141.5, 140.5, 135.9, 133.4, 131.0, 129.3, 128.5, 127.8, 127.6, 127.1, 126.8, 125.8, 125.2, 120.3, 119.9, 116.3, 116.1, 115.0, 114.8, 72.5, 69.7, 69.2, 68.5, 44.2, 41.0, 36.4.

MALDI-TOF-MS calcd for $C_{34}H_{31}F_2N_3O_2$ (M+H)⁺ 552.24, found 552.24.

EXAMPLE 8

Synthesis of 1-(8-amino-3,6-dioxaoctyl)-2-(2-fluorenyl)-4,5-bis(4-methoxyphenyl)imidazole (Compound 8 or Neurodazines 4)

A solution of 4-nitrophenyl chloroformate (0.8 g, 4 mmol) in CH₂Cl₂ was added to a Wang resin (1 mmol) in CH₂Cl₂ (9 mL) and pyridine (3 mL). After shaking for 12 h, the resin was washed with 10% dimethylformamide (DMF) in CH₂Cl₂. A solution of 2,2'-(ethylenedioxy)bisethylenediamine (1.5 g, 10 mmol) and diisopropylethylamine (0.6 g, 5 mmol) in DMF was added to the resin. After shaking for 12 h, the resin was washed with DMF. The resin (7 μmol), 2-fluorenecarboxaldehyde (13 mg, 0.07 mmol), ammonium acetate (22 mg, 0.28 mmol) and 4,4'-dimethoxy benzil (19 mg, 0.07 mmol) was placed in a reaction vial and suspended in acetic acid (300 μL). The reaction vial was placed in a heat block on a shaker at 100° C. The reaction vial was shaken for 5 h. The resin was filtered and washed with DMF, MeOH, and CH₂Cl₂ several times. The desired compound was cleaved from a solid support by treatment with trifluoroacetic acid (TFA) for 1.5 h. The crude product was directly purified by preparative RP-HPLC with a gradient of 5-100% CH₃CN in water (0.1% TFA) over 85 min.

Compound 8

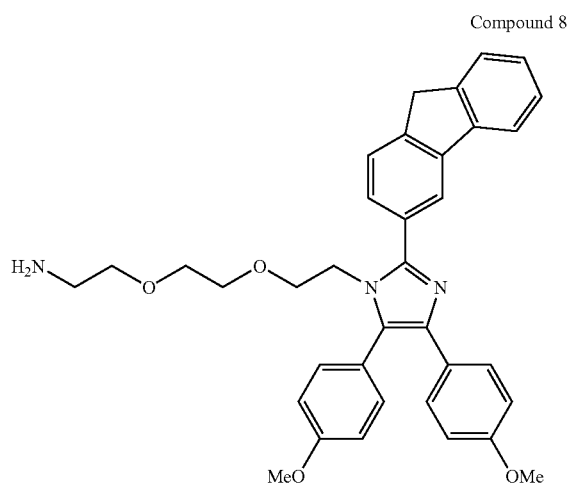

$^1$H NMR (500 MHz, CDCl$_3$) δ 8.04-7.93 (m, 3H), 7.80 (d, 1H, J=7.0 Hz), 7.62 (d, 1H, J=6.5 Hz), 7.45-7.32 (m, 5H), 7.09 (d, 2H, J=7.5 Hz), 6.79 (d, 2H, J=8.0 Hz), 4.14-4.07 (m, 2H), 4.02 (s, 2H), 3.83 (s, 3H), 3.69 (s, 3H), 3.32-3.18 (m, 8H), 2.58-2.52 (m, 2H).

$^{13}$C NMR (125 MHz, CDCl$_3$) δ 160.0, 158.3, 147.7, 144.0, 143.8, 141.9, 141.2, 137.1, 133.0, 130.4, 129.2, 128.2, 128.1, 127.8, 127.5, 126.4, 125.8, 123.6, 120.9, 120.5, 115.2, 114.1, 73.1, 70.3, 69.9, 69.2, 55.7, 55.5, 44.7, 41.6, 37.1.

MALDI-TOF-MS calcd for $C_{36}H_{37}N_3O_4$ (M+H)$^+$ 576.28, found 576.28.

EXAMPLE 9

Cell Culture and Small Molecule Screening

Murine myoblasts (C2C12) are usually cultured in RPMI 1640 or DMEM supplemented with 10% FBS, 50 units/mL penicillin and 50 μg/mL of streptomycin at 37° C. with 5% CO$_2$ in air atmosphere.

For the small molecule screen, the cultured C2C12 cells are seeded in a 96-well plate at a density of 10$^3$ cells per well in culture media. After 24 h, the culture media are replaced with differentiation media (RPMI 1640 or DMEM containing 1% FBS, 50 units/mL penicillin and 50 μg/mL of streptomycin). Test compounds are then added at a final concentration of 5-10 μM. After 96 h incubation, morphological changes of cells are observed by a light microscope (Nikon Eclipse TE2000) to detect neurite outgrowth characteristic of neuron differentiation. To ascertain neuron differentiation, the cells are washed with PBS and loaded FM1-43 (a final concentration: 2 μM, Molecular Probes) dissolved in Ringer buffer containing 100 mM KCl. After 5 min at room temperature, the cells are washed with Ringer buffer three times to remove excess FM1-43. Fluorescent intensity of the treated cells (excitation wavelength: 470 nm, emission wavelength: 540 nm) is read on a fluorescent microplate reader (SpectraMax GeminiEM, Molecular Devices).

The compounds that induce neurite formation or exhibit a high fluorescent intensity after treatment with FM1-43 in the presence of 100 mM KCl are initially selected as putative hits with a neuron differentiation inducing activity. The putative hits are further confirmed by Western blotting and immunocytochemical analyses of the expression of neuron-specific markers in compound-treated cells.

Western blotting analysis: Cells treated with compounds for 96 h are broken by lysis buffer (1 mM CaCl$_2$, 150 mM NaCl, 10 mM Tris [pH 7.4], 1% Triton X-100, 1 mM PMSF and one tablet of protease inhibitor cocktail per 20 ml buffer). Proteins are separated by 7.5% or 10% SDS-PAGE and transferred onto nitrocellulose membranes. The transferred membrane is treated with neuron-specific antibodies and then horseradish peroxidase-conjugated secondary antibody. The antibody-treated membrane is visualized by using the enhanced chemiluminescence kit (Amersham). Antibodies are used at the following dilutions: anti-neuron-specific βIII-tubulin mouse monoclonal antibody (1:1000), anti-neuron specific enolase chicken monoclonal antibody (1:500), anti-neurofilament 200 (phosphorylated and non-phosphorylated) clone C52 mouse monoclonal antibody (1:500), anti-skeletal myosin (fast) clone MY-32 mouse monoclonal antibody (1:500), anti-s-100 (B32.1) mouse monoclonal antibody (1:1000), and anti-choline acetyltransferase sheep polyclonal antibody (1:1000). The secondary antibodies used for Western blotting are horseradish peroxidase-conjugated goat anti-mouse IgG (1:2000), rabbit anti-chicken IgY (1:2000) and rabbit anti-sheep IgG (1:2000).

Immunocytochemical analysis: Cells treated with compounds for 96 h are fixed with PBS containing 4% paraformaldehyde and 0.1% triton x-100 for 10 min. The fixed cells are incubated with primary antibodies diluted in PBS containing 1% serum for 1 h. Cells are washed with PBS three times for 5 min and incubated with the appropriate secondary antibody diluted in PBS containing 1% serum for 1 h. Cells are washed with PBS three times for 5 min and incubated with Cy3-conjugated streptavidin diluted 1:100 in PBS for 0.5 h. Cells are washed with PBS five times for 5 min and mounted with aqueous mounting solution. Antibodies are used at the following dilutions: anti-neuron-specific βIII-tubulin mouse monoclonal antibody (1:500), anti-neuron specific enolase chicken monoclonal antibody (1:200), anti-neurofilament 200 (phosphorylated and non-phosphorylated) clone C52 mouse monoclonal antibody (1:400). Secondary antibodies are biotinylated goat anti-mouse IgG (1:500) or rabbit anti-chicken IgY (1:200). Cells are imaged by a fluorescence microscope (Nikon Eclipse TE2000 microscope).

EXAMPLE 10

Identification of Neurodazines as Hits that Induce Neuron Differentiation

An imidazole library of about 300 compounds is added at a final concentration of 5-10 μM. After 96 h incubation, neurite outgrowth is observed by a light microscope. Cells are then washed with PBS and loaded FM1-43 (a final concentration: 2 μM, Molecular Probes) dissolved in Ringer buffer containing 100 mM KCl. After 5 min at room temperature, cells are washed with Ringer solution three times to remove excess FM1-43. Fluorescent intensity (excitation wavelength: 470 nm, emission wavelength: 540 nm) is read on a fluorescent microplate reader (SpectraMax GeminiEM, Molecular Devices).

Once myoblasts are treated with Neurodazines, striking neurite outgrowth is observed between the neurodazine treated and untreated cells. In the control cells (treated with only DMSO), unchanged myoblasts are observed. In contrast, neurite formation is observed in the presence of 1 μM Neurodazines. Furthermore, cells treated with Neurodazines exhibit the strong fluorescent intensity of cells after treatment with FM1-43 in the presence of external depolarization caused by 100 mM KCl. In contrast, the control cells incubated with only DMSO show very low fluorescence signals. Among an imidazole library, Neurodazines 1-4 are found to induce the highest level of expression of neuron-specific markers, as measured by Western blot analysis and the largest degree of synaptic vesicle recycling in response to external depolarization, as measured by the dye FM1-43.

However, myogenic specific markers such as MyoD and myosin are not detected. Furthermore, astrocyte-specific marker such as s-100 is not detected, either. These results show that the differentiated neuron cells from myoblasts contain neither muscle nor astrocyte character.

EXAMPLE 11

Isolated Human Muscle Fibers are Differentiated into Neuron Cells by Treatment with Neurodazines Single fibers of human skeletal muscle are obtained as described previously (*In Vitro Cell Dev Biol Anim.* 2002, 38, 66). A sample of skeletal muscle is dissected from the abductor hallucis muscle. The sample is collected and transported in single fiber culture media (Ham's F-10 medium supplemented with 10% FBS, 2% chick embryo extract and 1.5 µg/mL amphotericin B). The muscle sample is incubated in 10 mL single fiber culture media containing 0.1% collagenase in a 50 mL Falcon™ tube for 1 h at 37° C. Bundles of muscle fibers are carefully dissected using a scalpel. The bundles are laid in a Petri dish containing 10 mL single fiber culture media with 0.1% collagenase at 37° C. for 5 h. Isolation of single muscle fibers is carried out by repeatedly triturating the muscle sample with a wide-mouthed Pasteur pipette. Isolated muscle fibers that have not undergone hypercontraction (which renders them unsuitable for plating in culture dishes) are placed in matrigel-coated 6-well plates at a density of three fibers per well. Fibers are plated in one drop of single fiber culture media and allowed to attach for 6 h and then 1 mL of media is added to the culture. After 24 h, the media are changed to single fiber culture media without amphotericin B.

After 5 days, populations of satellite muscle precursor cells migrate from the fiber and begin to proliferate. The fibers are removed by a Pasteur pipette and the cells are trypsinized with PBS containing 0.25% trypsin and 0.02% EDTA as required for further studies. To ascertain the neurogenic effects of compounds, cells are re-plated in 6well-plates at a density of 100 cells per well alone or in the presence of Neurodazines 1-4 (a final concentration: 1 µM, 5 µM or 20 µM). After 96 h, immunocytochemical analysis of compound treated cells using neuron-specific markers is performed or neurophysiological studies of compound treated cells are carried out using FM1-43, as described above.

The generation of neuron cells from human single muscle fibers is achieved by a two step incubation with Myoseverin and Neurodazines. First, the plated fiber is treated with Myoseverin (a final concentration: 10 µM) for 20 h to produce fiber fragments and cellular entities around the fiber exterior. The fiber is disrupted by repeated triturating in wide-mouth pipette to collect the fragments and cells. Second, the fibers are then re-plated in matrigel-coated 6-well plates at a density of 100 myotube fragments/mononucleated cells per well and treated with Neurodazine 1 or 2 (a final concentration: 1 µM) to induce neuron differentiation. After 96 h, neuron differentiation is ascertained by the observation of neurite outgrowth using a light microscope, increased fluorescent intensity after incubation with FM1-43 in the presence of 100 mM KCl or immunocytochemical analysis of the expressed neuron-specific markers.

What is claimed is:

1. A compound of Formula (I) having the following structure:

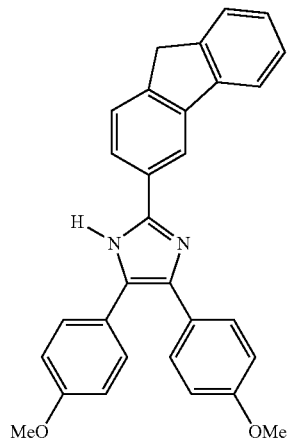

Formula (I)

2. A pharmaceutical composition inducing differentiation of myoblasts or muscle fibers into neuron cells comprising a compound of Formula (I) having the following structure:

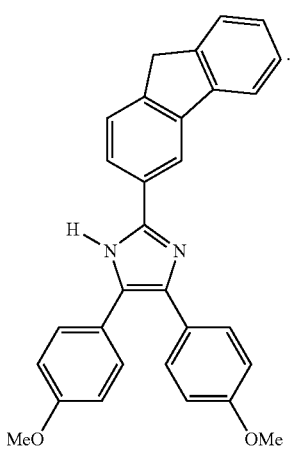

Formula (I)

3. A method of inducing differentiation of myoblasts and muscle fibers into neuron cells treating myoblasts and muscle fibers with a compound according to claim 1, whereby the myoblasts and muscle fibers differentiate into neuron cells.

4. The method according to claim 3, further comprising a step of detecting differentiation of myoblasts and muscle fibers into neuron cells.

5. The method according to claim 4, whereby differentiation of myoblasts and muscle fibers into neuron cells is detected by detecting expression of cell type-specific marker proteins.

6. The method according to claim 4, whereby differentiation of myoblasts and muscle fibers into neuron cells is detected by observing morphological changes of cells.

7. The method according to claim 4, whereby differentiation of myoblasts and muscle fibers into neuron cells is detected by detecting fluorescent intensity of cells after treatment with FM1-43 in the presence of 100 mM KCl.

8. The method according to claim 3, wherein the myoblast cell is isolated from a mouse.

9. The method according to claim 3, wherein the myoblast cell is isolated from a primate.

10. The method according to claim 3, wherein the myoblast cell is isolated from a human.

11. A screening method for identifying additional compound useful for inducing neuron differentiation, wherein myoblasts and muscle fibers are incubated with a compound according to claim 1 and detected.

* * * * *